April 9, 1946. W. E. LAMMERTS Plant Pat. 678
ROSE PLANT
Filed Jan. 30, 1945
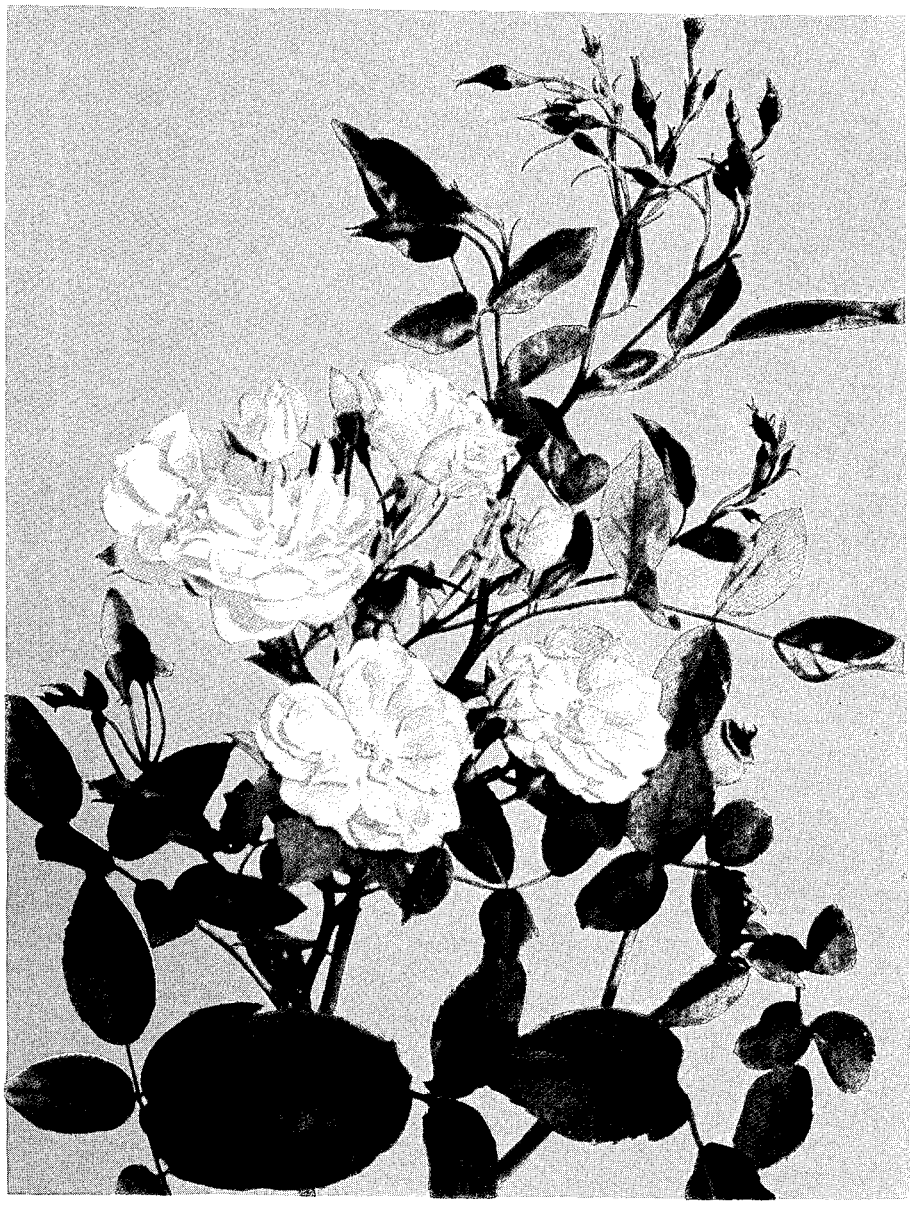
Inventor
W. E. Lammerts
By T. Robert Robb
His Attorney Patented Apr. 9, 1946

UNITED STATES PATENT OFFICE

678

ROSE PLANT

Walter E. Lammerts, West Los Angeles, Calif., assignor to Armstrong Nurseries, Inc., Ontario, Calif., a corporation of California Application January 30, 1945, Serial No. 575,226

1 Claim. (Cl. 47—61)

The present invention relates to a new and distinct variety of rose plant in the class of hybrid polyanthas embodying a new combination of characteristics, particularly a new color of flowers in this class.

This new variety was produced by the crossing of two well-known varieties, namely, "Mrs. Dudley Fulton" (Pl. Pat. #122) and the miniature "Tom Thumb" (Pl. Pat. #169), and it is characterized as to novelty by its dwarfish growth, compactness of the plant with glossy, mildew-resistant foliage of average size for dwarf polyantha, and exceptionally large trusses of bloom with all the flowers in the truss opening sufficiently close together to make an excellent and clear mass particularly desirable for garden decoration.

One of its dominating characters is that the flowers remain attractive during the period of fading reaction because of the absence of discoloration of the petals and because of the strong tendency for the petals to drop cleanly when they have passed full maturity. Further than this, the individual flowers are of larger size than the average for its class and are of a distinct new color tone for polyantha, of deep pink, hereinafter more specifically defined.

Asexual reproduction of this new variety shows the foregoing characteristics come true to form and are established.

The drawing shows specimens of this variety in various stages of development.

The following is a detailed description of this new variety, the color terminology being in accord with the Robert F. Wilson Horticultural Colour Chart, except where otherwise designated as taken from Ridgway's Color Standard:

Type: Dwarf; bush; seedling; for garden decoration.

Class: Hybrid polyantha.

Breeding: Seedlings.

*Seed parent.*—"Mrs. Dudley Fulton."

*Pollen parent.*—"Tom Thumb."

Propagation: Holds its distinguishing characteristics through succeeding propagations by budding, which is the only method tried up to the present.

*Flower*

Locality where grown: Ontario, California.

Flowers borne: Several to stem; in rounded cluster; on normal medium length stems for its class.

Quantity of bloom: Abundant; outdoors.

Continuity: Intermittent to nearly continuous.

Fragrance: Slight; tea to spicy.

Bud:

*Pedicel.*—Short; slender for polyanthas; medium erect; almost smooth; numerous, gland-tipped cilia, hairs; near Absinthe Green, Plate XXXI (Ridgway). Side exposed to sun tinted with near Cameo Brown, Plate XXVIII (Ridgway).

*Before calyx breaks.*—*Size*—small to medium for polyanthas. *Form*—short; pointed; ovoid with a conspicuous neck; with foliaceous appendages, tomentum, gland-tipped cilia, glandular bloom, on the surface of the bud; with slender, much cut, foliaceous parts extending beyond the tip of the bud equal to one-half or more of its length.

*As calyx breaks.*—*Color*—near China Rose, Plate 024. *Inner surface*—with fine, wooly tomentum. All margins of sepals lined with wooly tomentum and stipitate glands.

*As first petal opens.*—*Size*—small to medium for polyanthas. *Form*—very short; ovoid. *Color*—outside—near China Rose, Plate 024, changing toward base to near Mimosa Yellow, Plate 602/3. Inside—near China Rose, Plate 024, changing toward base to near Mimosa Yellow, Plate 602/3.

*Opening.*—Opens up well.

Bloom:

*Size.*—When fully open—medium to large for polyanthas, 1 inch to 2 inches.

*Petalage.*—Very double; from 20 to 26 petals; arranged regularly. Flower usually has 8 to 10 petaloids.

*Form.*—Cupped at first; becoming very flat; petals remaining at first very loosely cupped; becoming later, at maturity, very loosely rolled outward.

Petals: Thin; soft, with inside satiny.

*Shape.*—Outside—obovate; scalloped with apex flat, with 1 to 2 notches. Intermediate—obovate; scalloped with apex flat, with 1 to 2 notches. Inside—obovate to obovate-oblong; scalloped irregular with apex flat; with 1 notch.

This description of a newly opened flower was made from a rose grown outdoors in the month of October, 1944, at Ontario, California:

*Color.* — *Outside petal* — Outside surface: near China Rose, Plate 024/1, changing toward base to near Mimosa Yellow, Plate 602/3, usually with narrow stripe from base to near apex of Mimosa Yellow, Plate 602/3; inside surface: near China Rose, Plate 024/1, changing toward base to near Mimosa Yellow, Plate 602/3. *Intermediate petal*—outside surface: near China Rose, Plate 024/1, changing toward base to near Mimosa Yellow, Plate 602/3, usually with narrow stripe from base to near apex of Mimosa Yellow, Plate 602/3; inside surface: near China Rose, Plate 024/1, changing toward base to near Mimosa Yellow, Plate 602/3. *Inner petal*—outside surface: near China Rose, Plate 024/1, changing toward base to near Mimosa Yellow, Plate 602/3, usually with narrow stripe from base to near apex of Mimosa Yellow, Plate 602/3; inside surface: near China Rose, Plate 024/1, changing toward base to near Mimosa Yellow, Plate 602/3.

This description was made from a rose that was open for three days indoors in the month of October, 1944, at Ontario, California:

*Color.* — *Outside petal* — outside surface: near China Rose, Plate 024/2, changing toward base to near Mimosa Yellow, Plate 602/3, usually with stripe of near Mimosa Yellow, Plate 602/3, from base to apex; inside surface: near China Rose, Plate 024/2, changing toward base to near Mimosa Yellow, Plate 602/3. *Inside petal*—outside surface: near China Rose, Plate 024/2, changing toward base to near Mimosa Yellow, Plate 602/3, usually with stripe of near Mimosa Yellow, Plate 602/3, from base to apex; inside surface: near China Rose, Plate 024/2, changing toward base to near Mimosa Yellow, Plate 602/3.

*General color effect.*—Newly opened flower—near and between China Rose, Plate 024, and China Rose, Plate 024/1. Three days open—near and between China Rose, Plate 024/2, and China Rose, Plate 024/3.

*Behavior.* — Persist only slightly, fading brown. Fades more rapidly in hot weather.

*Flower longevity.*—On bush in garden—three days in October. Cut roses grown outdoors kept at living room temperatures—three days in October.

*Reproductive organs*

Stamens: Medium number; arranged irregularly about pistils, mixed with petaloids.

Filaments: Medium length for polyanthas; most with anthers.

Anthers: Small to medium for polyanthas; all open at once approximately; near Buttercup Yellow, Plate 5/2.

Pollen: Moderately abundant; yellow, but too minute to determine the shade or hue.

Pistils: Few.

Styles: Uneven; short to medium; medium heavy; bunched.

Stigma: White.

Ovaries: Most enclosed in, some protruding from, calyx.

Hips: Short; globular; with inconspicuous neck; near Chromium Green, Plate XXXII, (Ridgway), shading to near Verona Brown, Plate XXIX (Ridgeway) on side exposed to sun; moderately smooth; glandular; walls thick, fleshy.

Sepals: Falling soon; moderately long; spear-shaped; recurved. *Color.*—inside—near Rinnemanns Green, Plate XVIII (Ridgway), blushed with near Cameo Brown, Plate XXVIII (Ridgway); outside—near Rinnemanns Green, Plate XVIII (Ridgway).

Seeds: Very few.

Foliage:

*Leaves.*—Compound of 3 to 9 leaflets; normally abundant; small; moderately heavy; leathery; semi-glossy.

*Leaflets.*—Shape—ovate lanceolate, with apex acute. Base—round. Margin—irregularly serrate.

*Color.*—*Mature*—upper surface—near Forest Green, Plate XVII (Ridgway); under surface—near Parrot Green, Plate VI (Ridgway). *Young*—upper surface—near Parrot Green, Plate VI (Ridgway); under surface—near Asphodel Green, Plate XLI (Ridgway), tinted with near Army Brown, Plate XL (Ridgway).

*Rachis.*—Light. Upper side—grooved; glandular; under side—moderately smooth.

*Stipules.*—Short; narrow, with short points, turning out at an angle of more than 45°.

*Disease.*—Resistant to mildew.

Growth:

*Habit.*—Dwarf; bushy; much branched.

*Growth.*—Moderate for polyanthas.

*Canes.*—Moderately light to medium for polyanthas.

*Main stems.*—Near Absinthe Green, Plate XXXI (Ridgway). *Large prickles*—few; short; hooked downward; with long, narrow base. Color—near Cameo Brown, Plate XXVIII (Ridgway). *Small prickles*—none. *Hairs*—none.

*Branches.*—Near Absinthe Green, Plate XXXI (Ridgway), with side exposed to sun shaded with near Cameo Brown, Plate XXVIII (Ridgway). *Large prickles*—few; short; hooked downward; with narrow base. Color—near Cameo Brown, Plate XXVIII (Ridgway). *Small prickles*—none. *Hairs*—none.

*New shoots.*—Near Absinthe Green, Plate XXXI (Ridgway); side exposed to sun, near Cameo Brown, Plate XXVIII (Ridgway). *Large prickles.*—few; short; hooked downward; with narrow base. Color—near Cameo Brown, Plate XXVIII (Ridgway). *Small prickles and hairs*—none.

I claim:

A new and distinct variety of hybrid polyantha rose plant, characterized as to novelty by its dwarf and compact habits of growth with glossy, mildew-resistant foliage of average size for dwarf polyantha; unusually large trusses of bloom in which the flowers open sufficiently close together to make an excellent and clear mass of color; the absence of discoloration of the petals during the usual period of fading reaction, combined with the tendency of the petals to drop cleanly after attaining full maturity, thus materially prolonging the stage of attractiveness; the large size of the individual flowers for roses of its class; and the distinctly new color tone of said flowers for polyanthas, substantially as shown and described.

WALTER E. LAMMERTS.